United States Patent [19]
Cavero et al.

[11] Patent Number: 4,588,747
[45] Date of Patent: May 13, 1986

[54] 1,2,3,4-TETRAHYDRONAPHTHALENE DERIVATIVES USED AS ANTIGLAUCOMA AGENTS

[75] Inventors: Icilio Cavero, Creteil; Salomon Z. Langer, Paris, both of France

[73] Assignee: Synthelabo, Paris, France

[21] Appl. No.: 770,758

[22] Filed: Aug. 29, 1985

Related U.S. Application Data

[63] Continuation-in-part of Ser. No. 644,704, Aug. 27, 1984, abandoned.

[51] Int. Cl.$^4$ .............................................. A61K 31/16
[52] U.S. Cl. ..................................... 514/630; 514/913
[58] Field of Search ......................... 514/657, 913, 630

[56] References Cited
U.S. PATENT DOCUMENTS
4,442,126  4/1984  Beeley et al. ...................... 424/324

Primary Examiner—Douglas W. Robinson
Attorney, Agent, or Firm—Wegner & Bretschneider

[57] ABSTRACT 2-dipropylamino-5 or -7-formylamino-6-hydroxy-1,2,3,4-tetrahydronaphthalene and their pharmaceutically acceptable salts are useful as antiglaucoma agents.

5 Claims, No Drawings

1,2,3,4-TETRAHYDRONAPHTHALENE DERIVATIVES USED AS ANTIGLAUCOMA AGENTS

REFERENCE TO RELATED APPLICATION

This application is a continuation-in-part of copending application Ser. No. 644,704 filed Aug. 27, 1984 now abandoned.

DESCRIPTION OF THE INVENTION

A method of treating a patient having glaucoma is provided which comprises treating said patient with a compound of the formula I

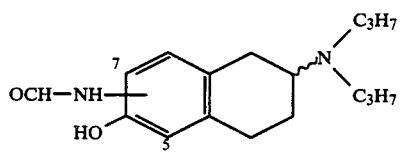

wherein the formylamino group is in the 5- or 7-position,
or a pharmaceutically acceptable salt thereof, said compound being in the form of the racemate or an enantiomer.

The compounds are preferably administered in the form of eye drops applied in a solution containing 0.1% to 2.0% of compound (I), with a representative example being 0.25%. The amount of the eye drops to be used will vary dependant upon the concentration. With 0.25% concentration being used, one drop per day may be used, or up to four drops per day.

These compounds (I) can be prepared in accordance with the methods described in European patent application No. 74 903.

EXAMPLE 1

Racemate of 2-dipropylamino-5-formylamino-6-hydroxy-1,2,3,4-tetrahydronaphthalene hydrobromide (a) 2-Dipropylamino-6-methoxy-1,2,3,4-tetrahydronaphthalene.

20 g of 6-methoxytetrahydronaphthalen-2-one, 20 ml of dipropylamine and 200 mg of para-toluenesulphonic acid are introduced into 300 ml of benzene under a nitrogen atmosphere. The mixture, which has become black, is then heated under reflux for 12 hours, the water of condensation being removed by azeotropic distillation. The solution is then concentrated to a volume of about 100 ml. For the hydrogenation, 150 ml of ethanol and 300 mg of PtO$_2$ are added thereto and hydrogenation is carried out, under a pressure of about 0.3 MPa, until the absorption has stopped.

After removal of the catalyst, the solvents are driven off under reduced pressure and the residual black oil is taken up in toluene and extracted with N hydrochloric acid. The hydrochloric acid solution is then neutralised with an alkali and extracted with toluene, the organic phase is dried and filtered on 200 g of neutral alumina, and elution is completed by means of methylene chloride. Concentration gives a virtually colorless oil.

(b) 2-Dipropylamino-6-methoxy-5(and 7)-nitro-1,2,3,4-tetrahydronaphthalene.

21 g of 2-dipropylamino-6-methoxy-1,2,3,4-tetrahydronaphthalene are added to 60 ml of trifluoroacetic acid, with simultaneous cooling of the mixture. 7 ml of nitric acid (d=2.42) are then added dropwise, the temperature being kept at about 0° C. The mixture is stirred for a further 10 minutes, the whole is poured into water and the insoluble material is extracted with methylene chloride; the organic phase is shaken with a solution of potassium carbonate and washed with water.

After drying and evaporation, the brown gum obtained is subjected to chromatography on a column of neutral alumina (800 g), elution being carried out with toluene. The less polar compound is the isomer nitrated in the 5-position. 9 g of each of the isomers are obtained. The compound nitrated in the 5-position melts at 198°–220° C. and the compound nitrated in the 7-position melts at 158°–160° C. (in the form of the hydrochlorides).

(c) 2-Dipropylamino-6-hydroxy-5-nitro-1,2,3,4-tetrahydronaphthalene hydrobromide.

9 g of 2-dipropylamino-6-methoxy-5-nitro-1,2,3,4-tetrahydronaphthalene are introduced into 100 ml of 48% hydrobromic acid and the mixture is heated under reflux for 2 hours. The acid is then driven off under reduced pressure and the residue is taken up three times in water, the water being evaporated off each time in order to remove any trace of acid. When recrystallised from water, the solid obtained forms a monohydrate which melts at 236° C. (with decomposition).

(d) 2-Dipropylamino-5-amino-6-hydroxy-1,2,3,4-tetrahydronaphthalene hydrobromide.

7 g of 2-dipropylamino-6-hydroxy-5-nitro-1,2,3,4-tetrahydronaphthalene hydrobromide are suspended in 250 ml of ethanol and hydrogenation is carried out at ambient temperature, in the presence of 1 g of 5% palladium-on-charcoal, under a pressure of about 0.3 MPa. The solvent is then evaporated off and the residue is triturated in diethyl ether. The product obtained melts at 215°–218° C. (with decomposition).

(e) 2-Dipropylamino-5-formylamino-6-hydroxy-1,2,3,4-tetrahydronaphthalene hydrobromide.

0.42 ml of acetic anhydride is added all at once to 2 ml of 98% formic acid, kept at 0° C., and the mixture is left at 0° C. for 15 minutes. Then, still using an ice-bath, 1.34 g of 2-dipropylamino-5-amino-6-hydroxy-1,2,3,4-tetrahydronaphthalene hydrobromide are introduced therein with a spatula and the whole is stirred for one hour at 0° C. After 50 ml of diethyl ether have been added and the solid has been filtered off, the latter is recrystallised from a 50/50 methanol/ethyl acetate mixture. This gives 1 g of the final product melting at 213° C. (with decomposition).

EXAMPLE 2

Racemate of 2-dipropylamino-7-formylamino-6-hydroxy-1,2,3,4-tetrahydronaphthalene hydrobromide (a) 2-Dipropylamino-7-amino-6-methoxy-1,2,3,4-tetrahydronaphthalene.

9 g of the 2-dipropylamino-6-methoxy-7-nitro-1,2,3,4-tetrahydronaphthalene obtained in accordance with Example 1(b) are introduced into 200 ml of ethanol, together with 1 g of Raney nickel. At ambient temperature, hydrogenation is carried out under pressure until the absorption has stopped. After evaporation of the solvent, an oil remains which is shown to oxidise fairly readily in air.

(b) 2-Dipropylamino-7-amino-6-hydroxy-1,2,3,4-tetrahydronaphthalene dihydrobromide.

The product obtained above is introduced in 100 ml of 48% hydrobromic acid, the mixture is heated under reflux for 10 hours and the acid is then driven off under reduced pressure and subsequently removed completely by distillation with a toluene/ethanol mixture in a rotary evaporator. After recrystallisation from isopropyl alcohol, the dihydrobromide melts at 250° C. (with decomposition).

(c) 2-Dipropylamino-7-amino-6-hydroxy-1,2,3,4-tetrahydronaphthalene monohydrobromide.

A solution of 5 ml of Amberlite LA2 resin in 50 ml of petroleum ether is added to a solution of 3 g of the dihydrobromide obtained in (b) above in 50 ml of water. The mixture is shaken for 15 minutes at ambient temperature and the aqueous phase is separated off and evaporated to dryness in order to isolate the crude monhydrobromide, in an amorphous and coloured form, which is used as such for the formylation.

(d) 2-Dipropylamino-7-formylamino-6-hydroxy-1,2,3,4-tetrahyronaphthalene hydrobromide.

0.7 ml of acetic anhydride is added to 3 ml of 98% formic acid, kept at 0° C., and the whole is left for 15 minutes at 0° C. 2.2 g of 2-dipropylamino-7-amino-6-hydroxy-1,2,3,4-tetrahydronaphthalene hydrobromide are then added thereto and the mixture is then stirred for one hour at 0° C. After 50 ml of diethyl ether have been added and the solid has been filtered off, the latter is recrystallised from a 50/50 methanol/ethyl acetate mixture. This gives 1 g of the final product melting at 213° C. (with decomposition).

EXAMPLE 3

Enantiomers of 2-dipropylamino-5-formylamino-6-hydroxy-1,2,3,4-tetrahydronaphthalene hydrobromide.

(a) 2-Amino-6-methoxy-1,2,3,4-tetrahydronaphthalene hydrochloride.

A mixture of 10 g of 6-methoxy-tetrahydronaphthalen-2-one in 150 ml of benzene and 5.9 ml of benzylamine is heated under reflux for two hours with 100 mg of para-toluenesulphonic acid under a nitrogen atmosphere. The water of condensation is removed by azeotropic distillation. The mixture is concentrated to a volume of 100 ml and subjected to catalytic hydrogenation, in the presence of 100 mg of $PtO_2$, under a pressure of 0.35 MPa and at ambient temperature. The catalyst is removed by filtration and 4.7 ml of 12N hydrochloric acid are added to the filtrate.

A second hydrogenation is then carried out, in the presence of 1 g of palladium-on-charcoal, at about 60° C. and at a pressure of 0.35 MPa.

The catalyst is removed, the solvents are driven off under reduced pressure and the product formed is recrystallised from isopropyl alcohol; the product melts at 254° C. The hydrochloride is converted to the base by a known manner, for example by evaporating the organic phase of a mixture of methylene chloride, water and sodium hydroxide, into which the hydrochloride has been introduced.

(b) Separation of the enantiomers of 2-amino-6-methoxy-1,2,3,4-tetrahydronaphthalene.

A solution of 6 g of L(−)dibenzoyltartaric acid in 100 ml of ethanol is added rapidly to 5.5 g of the racemic amine (base), obtained as indicated above, in solution in 100 ml of ethanol. The heterogeneous medium thus obtained is concentrated under reduced pressure, the concentrate is taken up in diethyl ether and, after filtration and drying, 11 g of a salt which contains 0.5 mol of L(−)dibenzoyltartaric acid are collected. This salt is recrystallised twice from ethanol containing 30% of water. The product obtained melts at 220°-221° C. By converting it to the hydrochloride, an optically active salt is obtained which melts at 254° C. (with decomposition) and has an optical rotation of $[\alpha]_D^{25} = -73°$ (c=1, MeOH).

To isolate the other enantiomer, the ethanolic mother liquors from the recrystallisation of the L(−)dibenzoyltartrate are concentrated, the base form of the amine is re-formed and, after it has been extracted, the D(+)dibenzoyltartrate thereof is precipitated by adding the corresponding acid. After recrystallisation the D(+)dibenzoyltartrate melts at 220°-221° C. By formation of the hydrochloride, an optically active salt is obtained which has an optical rotation of $[\alpha]_D^{25} = +73°$ (c=1, MeOH).

(c) (−)-2-dipropylamino-6-methoxy-1,2,3,4-tetrahydronaphthalene hydrochloride.

15 ml of saturated solution of potassium carbonate and then 9 ml of iodopropane are added to 1.9 g of the laevorotatory hydrochloride obtained as indicated above, in suspension in 20 ml of benzene. The mixture is stirred at reflux temperature for 72 hours. The organic phase is then diluted with diethyl ether, and the hydrochloride is formed by adding a solution of hydrogen chloride in diethyl ether and isolated in the usual manner. It melts at 154° C. and has an optical rotation of $[\alpha]_D^{25} = -2.2°$ (c=1, MeOH).

(d) (−)-2-Dipropylamino-5-formylamino-6-hydroxy-1,2,3,4-tetrahydronaphthalene hydrobromide.

The procedure of example 1(b), (c), (d) and (e) is followed, using the laevorotatory enantiomer prepared as indicated above instead of the racemic mixture. The 6-methoxy-5-nitro intermediate hydrochloride has an optical rotation of $[\alpha]_D^{25} = -140°$ (c=1, MeOH).

The 6-hydroxy-5-amino intermediate hydrobromide has an optical rotation of $[\alpha]_D^{25} = -32°$ (c=1, MeOH).

The hydrobromide of the final laevorotatory enantiomer has an optical rotation of $[\alpha]_D^{25} = -48°$ (c=1, MeOH).

(e) (+)-2-Dipropylamino-5-formylamino-6-hydroxy-1,2,3,4-tetrahydronaphthalene hydrobromide.

The procedure of example 1(b), (c), (d) and (e) is followed, using the dextrorotatory enantiomer prepared as indicated above instead of the racemic mixture. The optical rotation of the intermediates and final compounds are exactly opposite to those indicated respectively under (d) above, especially the final dextrorotatory hydrobromide has an optical rotation of $[\alpha]_D^{25} = +48°$ (c=1, MeOH).

EXAMPLE 4

EXAMPLE 4

Enantiomers of 2-dipropylamino-7-formylamino-6-hydroxy-1,2,3,4-tetrahydronaphthalene hydrobromide.

(a) (−)-2-Dipropylamino-7-formylamino-6-hydroxy-1,2,3,4-tetrahydronaphthalene hydrobromide.

The procedure of example 2 is followed, using the laevorotatory 6-methoxy-7-nitro intermediate previously isolated, which has an optical rotation of $[\alpha]_D^{25} = -76°$ (c=1, MeOH).

The 6-hydroxy-7-amino intermediate hydrobromide has an optical rotation of $[\alpha]_D^{25} = -70°$ (c=1, MeOH).

The hydrobromide of the final laevorotatory enantiomer has an optical rotation of $[\alpha]_D^{25} = -68°$ (c=1, MeOH).

(b) (+)-2-Dipropylamino-7-formylamino-6-hydroxy-1,2,3,4-tetrahydronaphthalene hydrobromide.

The procedure of example 2 is followed, using the dextrorotatory 6-methoxy-7-nitro intermediate previously isolated, which has an optical rotation of $[\alpha]_D^{25} = +76°$ (c=1, MeOH).

The 6-hydroxy-7-amino intermediate hydrobromide has an optical rotation of $[\alpha]_D^{25} = +70°$ (c=1, MeOH).

The hydrobromide of the final dextrorotatory enantiomer has an optical rotation of $[\alpha]_D^{25} = +68°$ (c=1, MeOH).

EXAMPLE 5

The compounds were tested as to their action on intraocular pressure of rabbits.

Drops were made by dissolving a sufficient quantity of the compounds (in form of the hydrobromide salts) in distilled water to give 1 percent solutions of each compound. A dose of 50 µl of each solution was administered topically to the left eye of the animals. Control animals received only a saline solution.

The intraocular pressure was measured just before administration of the drugs, and then each hour thereafter. The intraocular pressure was decreased to 75 percent of the initial value between 2 and 3 hours after administration. The initial value (100 percent) was reached again 6 hours after administration. The pressure in the contralateral eye was also depressed (85 percent of the initial value) at ½ hour after administration and remained depressed for 3 hours.

The pupil diameter was not significantly influenced.

We claim:

1. A method of treating glaucoma in a patient, which comprises topically administering to said patient an amount effective to reduce intraocular pressure of a compound of formula I

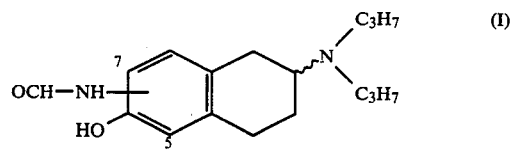

wherein the formylamino group is in the 5- or 7-position, and said compound is in the form of the racemate or one of the enantiomers thereof, or a pharmaceutically acceptable salt thereof.

2. A method according to claim 1, wherein said compound is 2-dipropylamino-5-formylamino-6-hydroxy-1,2,3,4-tetrahydronaphthalene or a pharmaceutically acceptable salt thereof.

3. A method according to claim 1, wherein said compound is 2-dipropylamino-7-formylamino-6-hydroxy-1,2,3,4-tetrahydronaphthalene or a pharmaceutically acceptable salt thereof.

4. An eye drop for the treatment of glaucoma through topical application of said eye drop to the eye of a patient suffering from glaucoma, comprising a therapeutically effective amount of a compound of formula I

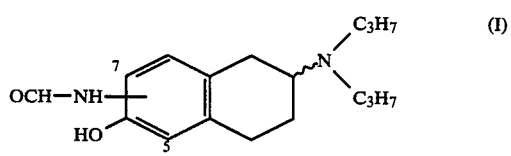

wherein the formylamino group is in the 5- or 7-position, and said compound is in the form of the racemate or one of the enantiomers thereof, or a pharmaceutically acceptable salt thereof, and a solvent for said compound which is suitable for topical application to the eye of a patient.

5. An eye drop according to claim 4 wherein said effective amount is from about 0.1% to about 2.0% of said eye drop.

* * * * *